US00PP18527P2

(12) United States Plant Patent
Klemm

(10) Patent No.: US PP18,527 P2
(45) Date of Patent: Feb. 26, 2008

(54) ***SUTERA* PLANT NAMED 'KLESG05179'**

(50) Latin Name: *Sutera grandiflora*
Varietal Denomination: KLESG05179

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/583,601

(22) Filed: Oct. 19, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Sutera* plant named 'KLESG05179', characterized by its compact, rounded and trailing growth habit; freely branching habit; early and freely flowering habit; and large white-colored flowers.

1 Drawing Sheet

Botanical designation: *Sutera grandiflora.*
Cultivar denomination: 'KLESG05179'.

BACKGROUND OF THE INVENTION

The present invention relates to a new and distinct cultivar of *Sutera,* botanically known as *Sutera grandiflora,* and hereinafter referred to by the name 'KLESG05179'.

The new *Sutera* is a product of a planned breeding program conducted by the Inventor in Stuttgart, Germany. The objective of the breeding program is to create new compact *Sutera* cultivars with large and numerous flowers.

The new *Sutera* originated from a cross-pollination made by the Inventor in Stuttgart, Germany in August, 2003 of a proprietary selection of *Sutera grandiflora* identified as code number SG 001, not patented, as the female, or seed, parent with a proprietary selection of *Sutera grandiflora* identified as code number V 036, not patented, as the male, or pollen, parent. The cultivar KLESG05179 was discovered and selected by the Inventor as a flowering plant within the progeny of the stated cross-pollination in a controlled environment in Stuttgart, Germany in June, 2004.

Asexual reproduction of the new *Sutera* by terminal cuttings in a controlled environment in Stuttgart, Germany since September, 2004, has shown that the unique features of this new *Sutera* are stable and reproduced true to type in successive generations.

SUMMARY OF THE INVENTION

The cultivar KLESG05179 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'KLESG05179'. These characteristics in combination distinguish 'KLESG05179' as a new and distinct cultivar of *Sutera:*

1. Compact, rounded and trailing growth habit.
2. Freely branching habit.
3. Early and freely flowering habit.
4. Large white-colored flowers.

Plants of the new *Sutera* can be compared to plants of the parent selections. Plants of the new *Sutera* differ primarily from plants of the parent selections in plant size as plants of the new *Sutera* are more compact than plants of the parent selections. In addition, plants of the new *Sutera* have larger flowers than plants of the male parent selection.

Plants of the new *Sutera* can be compared to plants of the *Sutera grandiflora* cultivar KLESU03187, not patented. In side-by-side comparisons conducted in Stuttgart, Germany, plants of the new *Sutera* differed from plants of the cultivar KLESU03187 in the following characteristics:

1. Plants of the new *Sutera* were more compact than and not as vigorous as plants of the cultivar KLESU03187.
2. Plants of the new *Sutera* had larger flowers than plants of the cultivar KLESU03187.

BRIEF DESCRIPTION OF THE PHOTOGRAPH

The accompanying colored photograph illustrates the overall appearance of the new *Sutera,* showing the colors as true as it is reasonably possible to obtain in colored reproductions of this type. Colors in the photograph may differ slightly from the color values cited in the detailed botanical description which accurately describe the colors of the new *Sutera.* The photograph comprises a close-up view of a typical flowering plant of 'KLESG05179'.

DETAILED BOTANICAL DESCRIPTION

The photograph and following observations, measurements and values describe plants grown in Stuttgart, Germany in a glass-covered greenhouse during the spring and summer and under conditions which closely approximate commercial production. During the production of the plants, day temperatures ranged from 20° C. to 28° C., night temperatures ranged from 16° C. to 18° C. and maximum light levels were 60,000 lux. Plants were pinched one time and were about eleven weeks old when the photograph and the description were taken. In the description, color references are made to The Royal Horticultural Society Colour Chart, 1995 Edition, except where general terms of ordinary dictionary significance are used.

Botanical classification: *Sutera grandiflora* cultivar KLESG05179.

Parentage:

*Female, or seed, parent.*—Proprietary selection of *Sutera grandiflora* identified as code number SG 001, not patented.

*Male or pollen parent.*—Proprietary selection of *Sutera grandiflora* identified as code number V 036, not patented.

Propagation:

*Type.*—By terminal vegetative cuttings.

*Time to initiate roots, summer.*—About seven to ten days at temperatures of 20° C.

*Time to initiate roots, winter.*—About two weeks at temperatures of 20° C.

*Time to develop roots, summer.*—About 10 to 13 days at temperatures of 20° C.

*Time to develop roots, winter.*—About 14 to 17 days at temperatures of 20° C.

*Root description.*—Fine, fibrous; pale white in color.

*Rooting habit.*—Freely branching; moderately dense.

Plant description:

*Plant form and growth habit.*—Compact, rounded and trailing plant habit.

*Branching habit.*—Freely branching, about ten to twelve lateral branches develop per plant; pinching enhances branching.

*Plant height.*—About 9 cm.

*Plant diameter* (*area of spread*).—About 20 cm.

Lateral branch description:

*Length.*—About 5 cm to 10 cm.

*Diameter.*—About 3 mm.

*Internode length.*—About 1.2 cm.

*Texture.*—Sparsely pubescent.

*Color.*—138B.

Foliage description:

*Arrangement.*—Opposite, simple.

*Length.*—About 1.2 cm.

*Width.*—About 1.6 cm.

*Shape.*—Cordate.

*Apex.*—Obtuse.

*Base.*—Obtuse with cordate tendencies.

*Margin.*—Crenate.

*Texture, upper and lower surfaces.*—Sparsely pubescent.

*Venation pattern.*—Palmate.

*Color.*—Developing, upper surface: 137B. Developing, lower surface: 137C. Fully expanded foliage, upper surface: 139A; venation, 138B. Fully expanded foliage, lower surface: 137B; venation, 138B.

*Petiole.*—Length: About 2 mm to 5 mm. Diameter: About 2 mm. Texture, upper and lower surfaces: Smooth, glabrous. Color, upper and lower surfaces: 138A.

Flower description:

*Flower arrangement.*—Single flowers arranged on terminal racemes. Freely flowering habit with usually about 17 to 25 open flowers and flower buds per lateral branch. Flowers face upright and outwardly. Flowers not fragrant. Flowers not persistent.

*Natural flowering season.*—Plants begin flowering about four to six weeks after planting and flower intermittently from the spring through autumn Germany. Flowers last about five days on the plant.

*Flower diameter.*—About 2.5 cm.

*Flower length* (*height*).—About 1.2 cm.

*Flower tube length.*—About 1 cm.

*Flower throat diameter.*—About 5 mm.

*Flower tube diameter.*—About 1 mm.

*Flower bud.*—Length: About 5 mm. Diameter: About 3 mm. Shape: Obovate. Color: 145B.

*Petals.*—Quantity per flower: Corolla consists of five petals fused at the base. Lobe length from throat: About 1 cm. Lobe width: About 7 mm. Shape: Roughly spatulate. Apex: Obtuse, rounded. Base: Fused. Margin: Entire. Texture, upper and lower surfaces: Smooth, glabrous; velvety. Color: When opening, upper and lower surfaces: 155D. Fully opened, upper and lower surfaces: 155D. Throat: 14B. Tube: 145C.

*Sepals.*—Appearance: Five sepals fused into a tubular calyx. Length: About 4 mm. Width: About 1 mm. Shape: Lanceolate. Apex: Acute. Margin: Entire. Texture, upper and lower surfaces: Smooth, glabrous. Color, upper and lower surfaces: 138A.

*Peduncles.*—Length: About 5 cm. Diameter: About 3 mm. Angle: Erect. Strength: Moderately strong. Texture: Smooth, glabrous. Color: 137C.

*Pedicels.*—Length: About 5 mm. Diameter: About 1 mm. Angle: About 30° from stem axis. Strength: Moderately strong. Texture: Smooth, glabrous. Color: 138A.

*Reproductive organs.*—Androecium: Stamen number: About four. Anther shape: Elliptic. Anther length: Less than 1 mm. Anther color: 15A. Amount of pollen: Moderate. Pollen color: 15A. Gynoecium: Pistil length: About 1 cm. Style length: About 1 cm. Style color: 145B. Stigma appearance: Elliptic. Stigma color: 145B. Ovary color: 145B.

*Seeds/fruits.*—Seed and fruit production have not been observed.

Temperature tolerance: Plants of the new *Sutera* have been observed to tolerate temperatures from about 5° C. to about 35° C.

Pathogens/pest resistance: Plants of the new *Sutera* have not been shown to be resistant to pathogens and pests common to *Sutera*.

It is claimed:

1. A new and distinct *Sutera* plant named 'KLESG05179' as illustrated and described.

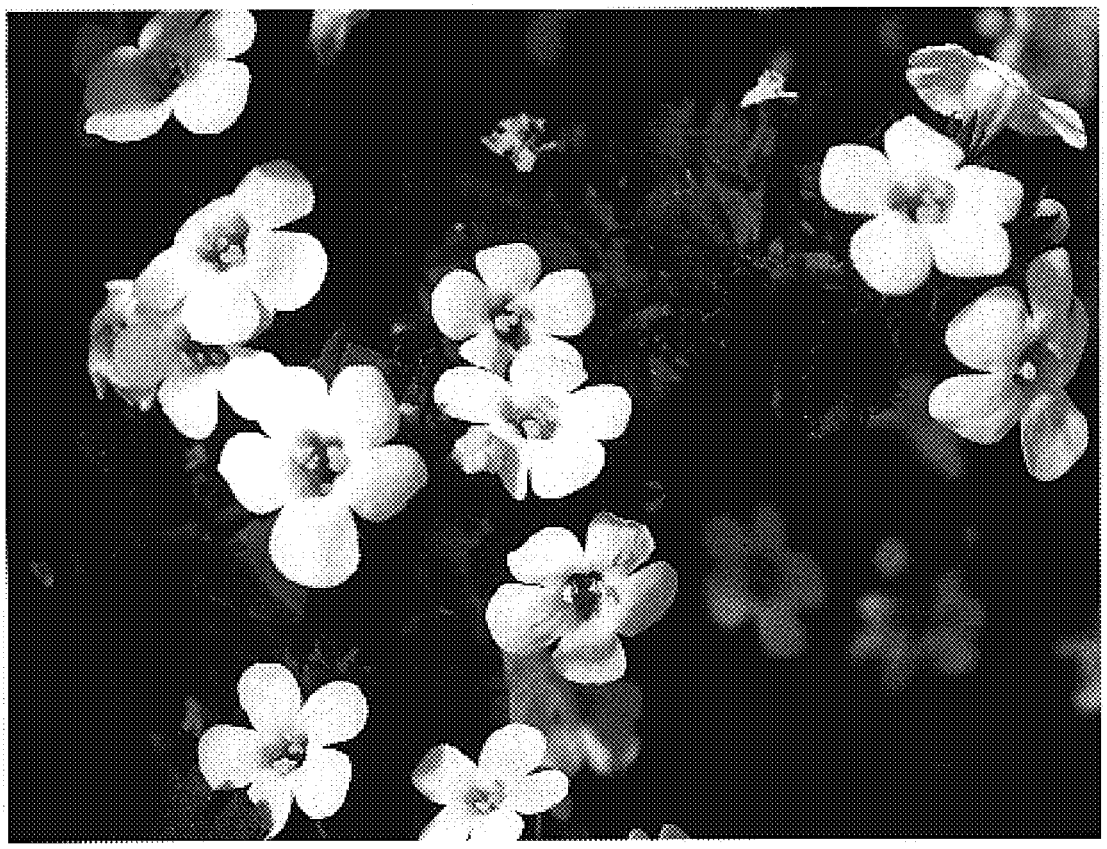

* * * * *